(12) United States Patent
Girsh

(10) Patent No.: US 6,974,796 B1
(45) Date of Patent: Dec. 13, 2005

(54) THERAPEUTIC COMPOSITIONS FOR TREATMENT OF A DAMAGED TISSUE

(76) Inventor: Leonard S. Girsh, 3360 S. Ocean Blvd., Palm Beach, FL (US) 33480

( * ) Notice: Subject to any disclaimer, the term of this patent is extended or adjusted under 35 U.S.C. 154(b) by 23 days.

(21) Appl. No.: 09/639,859

(22) Filed: Aug. 16, 2000

Related U.S. Application Data

(60) Provisional application No. 60/149,338, filed on Aug. 17, 1999.

(51) Int. Cl.$^7$ ............... A61K 38/16; A61K 31/715; G01N 33/92
(52) U.S. Cl. ............... 514/8; 514/54; 530/356; 530/395; 562/433; 436/71; 436/89; 424/9.1
(58) Field of Search ............... 562/433; 514/8, 514/54; 530/356, 395; 436/71

(56) References Cited

U.S. PATENT DOCUMENTS

| | | | |
|---|---|---|---|
| 5,236,899 A | * | 8/1993 | Durette ............... 514/11 |
| 5,753,211 A | * | 5/1998 | Garson et al. ............... 424/61 |
| 6,479,059 B2 | * | 11/2002 | Montanari et al. ............... 424/401 |

FOREIGN PATENT DOCUMENTS

| WO | WO 92/21752 | * 12/1992 |
|---|---|---|

OTHER PUBLICATIONS

Henschen et al., Ann N. Y. Acad. Sc. 408, 28-43 (1983).*
Wayman et al., Neurodevelopmental outcome of young children with extrahepatic biliary atresia 1 year after transplantation. *The Journal of Pediatrics*, 31(6), 894-898 (Dec. 1977.
Neocate Product Information Sheet, downloaded from www.shsweb.co.uk on Jul. 20, 2000.

* cited by examiner

*Primary Examiner*—Jon Weber
*Assistant Examiner*—Chih-Min Kam
(74) *Attorney, Agent, or Firm*—DLA Piper Rudnick Gray Cary US LLP

(57) ABSTRACT

The present invention relates to a therapeutic composition and uses thereof for treatment of damaged tissue, wherein the composition comprises at least one extracellular matrix compound, at least one polar surface active lipid, and a plurality of amino acids having a molar ratio which is characteristic of human breast milk protein; and further comprises a fatty acid, gamma-amino butyric acid or L-carnitine.

19 Claims, 1 Drawing Sheet

THERAPEUTIC COMPOSITIONS FOR TREATMENT OF A DAMAGED TISSUE

This application is a continuation of U.S. Patent Application No. 60/149,338 filed Aug. 17, 1999, which is hereby incorporated by reference herein in its entirety.

FIELD OF THE INVENTION

The present invention relates to a non-invasive medical therapy and compositions for avoiding organ transplantation, reducing rejection of transplanted organs, or treating organs under consideration for replacement by transplant, and otherwise treating aged, diseased or abnormal tissues and organs. The composition and methods of the invention may also be used to treat dermatological disorders, gastrointestinal disorders, ophthalmic disorders (such as diseased corneas), bacterial infections, respiratory disorders, tracheobronchial disorders, and various disorders related to aging. The present invention involves administering to a patient a therapeutic formulation comprising a free L-amino acid profile simulating or replicating the proteins normally present in healthy tissue that is now diseased or is a transplanted tissue. The invention also relates to therapy involving administration of therapeutic formulations comprising free L-amino acids in which the molar ratios of the amino acids correspond to the ratios of amino components in a medication that is useful for treating a disease. By simultaneous administration of the various components of one of the therapeutic formulations, the components are able to work synergistically to restructure diseased tissue and organ.

BACKGROUND

The present invention is useful for the treatment of many disorders, particularly tissue or organ failure (such as kidney or liver failure), corneal disorders, gastrointestinal disorders, and dermatological disorders. At present, many of the methods of therapy for these disorders involve invasive surgical methods, such as organ transplant in the case of extreme tissue damage. Organ transplantation involves many risks, such as complications resulting from the anesthesia and surgical procedures, side effects from medications, such as cyclosporin, which help prevent organ rejection, and the risks of blood borne pathogens or shock if transfusions are needed. Moreover, organ transplantation is very costly. The present invention functions to treat disorders with a therapy that has minimal risk of complications, low cost, and no serious side-effects.

The present invention concerns useful therapeutic formulations having L-amino acids present in molar ratios corresponding to either (1) the ratio of the amino constituents in normal tissue or normal organs, or (2) the constituents found in a medicinal compound useful for treating a medical disorder. Furthermore, Applicants have discovered that relatively low amounts of this therapeutic formulation comprised of L-amino acids, such as a daily intake of about 10 grams or less for an adult, are sufficient for therapeutic effect. The invention can be used with many medical disorders, preferably to avert the need for organ transplants, to treat the biological rejection of a transplanted organ, or prophylactically after transplantation before rejection occurs to reduce the risk of organ rejection. In one embodiment, the therapeutic formulations of the invention are administered for pre-operative optimal care where considerations for surgery have not been finalized. In one embodiment, the therapeutic formulation components simulate the chemical components in cyclosporin.

Elemental feedings containing free amino acids are known as substitutes for milk allergies or milk intolerance, such as in infantile asthma, eczema, or colic. The following articles disclose such uses, all of which are incorporated in their entirety herein by reference: *Beyond hydrolysates: Use of L-amino acid formula in resistant dietary protein-induced: intestinal disease in infants*, Lake, A. M., *J. Pediatrics*, 131:658–660 (1997); *Intolerance to protein hydrolsate infant formulas: An under-recognized cause of gastrointestinal symptoms in infants*, Mack, D. R, Antonson, D. L., Corkins, M. R., Perry, D., and Kruger, R., *J. Pediatrics*, 131: 741–744 (1997); *Allergy to extensively hydrolyzed cow milk proteins in infants: Identification and treatment with an amino acid-based formula*, DeBoissieu, D., Matarazzo, P., and Dupont, C., *J. Pediatrics*, 131:741–744 (1997); and *Efficacy and safety of hydrolyzed cow milk and amino acid-derived formula in infants with cow milk allergy*, Solauri, E., Sutas, Y., Makinen-Kilgunen, S., Oja, S. S., Isosomppi, and R., Turjanmaa, K., *J. Pediatrics*, 131: 550–557 (1997). Elemental feedings are also known to be useful for treatment of gastrointestinal conditions, such as Crohn's disease (regional ileitis), as noted in the following article, which is incorporated herein in its entirety by reference: *Treatment of active Crohn's disease by exclusion diet: East Anglian multicentre controlled trial*, Riordan, A. M., Hunter J. O., Cowan, R. E., Crampton, J. R., Davidson, A. R., Dickinson, R. J., Dronfield, M. W., Ellows, I. W., Hishon, and S., Kerrigan, G. N., et al., *Lancet*, 342 (8880): 1131–34 (Nov. 6, 1993). In the present invention, much smaller dosages of L-amino acids are used than are found in elemental feedings. Furthermore, the inventive compositions contain specific molar ratios of L amino acids for a given disease or to mimic therapy with a given medicament.

The present invention is particularly useful for the medical treatment of congenital biliary atresia, which is the most common cause for pediatric liver transplantation. Congenital biliary atresia has been a fatal disease if not treated surgically with liver transplantation and the Kasai procedure. Past research suggests that congenital biliary atresia is caused by the following: (1) hypersensitivity immunopathy; (2) viral infection—hepatic; and (3) inflammation due to (1) and (2). Eosinophiles present in early stages are suggestive of possible hypersensitivity. In the article entitled *Contribution of Hepatic Parenchymal and Nonparenchymal Cells to Hepatic Fibrogenesis in Biliary Atresia*, Ramm, Grant A., Nair, Visalini G., Bridle, Kim R., and Shepherd, Ross, W., *American Journal of Pathology*, 13(2)L 27–35 (August 1998), which is hereby incorporated herein in its entirety by reference, it is disclosed that extrahepatic congenital biliary atresia is a severe neonatal liver disease resulting from a sclerosing cholangiopathy of unknown etiology. Although biliary obstruction may be surgically improved by a "Kasai" hepatoportoenterostomy, most patients still develop progressive hepatic fibrosis and cirrhosis. Although the source of increased collagen deposition is unclear, an article entitled *Prognostic value of serum procollagen III peptide and type IV collagen in patients with congenital biliary atresia*, Kobayashi H., Mayano, T., Horikoshi, K., and Tokita A., *J. of Ped. Surgery*, 33(1):112–4 (January 1998), which is hereby incorporated herein in its entirety by reference, discloses that progressive hepatic fibrosis, in spite of a successful Kasai procedure, is a major problem in patients with congenital biliary atresia. N-terminal procollagen-III peptide (PIIP) (which is a marker of fibrogenesis, and therefore, of ongoing inflammation), and type IV collagen (found in basement membrane extracellular matrix), were measured in patients with congenital biliary atresia to determine their potential as prognostic markers.

*Long-term follow-up of patients with congenital biliary atresia successfully treated with hepatic portoenterostomy: The importance of sequential treatment*, Lopez-Santamaria M., Gamez M., Marcia J. Diez-Pardo, J., Diaz, M., Leal, N., Lobato R., Martinez, L., Hierro, L., Camarena C., De La Vega A., Frauca E., Jara P., Barrocal, T., Prieto, C. Coretes P., and Tovar, J., *Ped. Surgery International* 13(5–6):327 (July 1998), which is hereby incorporated herein in its entirety by reference, discloses long-term follow-up of patients with congenital biliary atresia who have been treated with hepatic portoenterostomy. As to the importance of sequential treatment, the authors concluded that the natural outcome of extrahepatic biliary atresia is toward fibrosis, and cirrhosis, even in those cases successfully treated with hepatic portoenterostomy (HPE).

*Urinary 7alpha-hydroxy-3-oxochol-4-en-24-oic and 3-oxochola-4,6-dien-24-oic acids in infants with cholestasis*, Kimura, A., Suzuki, M., Murai, T., Kurosawa, T., Tohma, M., Sata M., Inoue, T., Hoshiyama, A., Nakashima E., Yamashita, Y., Fujisawa, T., and Kate, H., *J. of Hepatology*, 28(2):270–9 (February 1998), which is hereby incorporated herein in its entirety by reference, discloses that urinary 3-oxo-delta4 bile acids have been detected in infants who ultimately died of liver disease. The results reported in this article suggest that an increase in the 7 alpha-hydroxy-3-oxochol-4-en-24-oic acid and 3-oxochola-4,6-dien-24-oic acid in the urine of patients with hepatobiliary disease indicates a poor prognosis.

*The first cooperative living-related donor liver transplantation performed by two separate institution teams: The Kanaqawa Liver Transplantation Program*, Ohhama, Y., Shinkai, M., Fujita, S., Nishi, T., Yamamoto, H., Torigai, K., Takemiya, S., Sugimasa, Y., Akaike, M., and Tanabe, H., *Surgery Today*, 28(2): 173–7 (1998), which is hereby incorporated herein in its entirety by reference, is a study of living-related donor liver transplantations. The study involves five children with congenital biliary atresia who were given partial liver grafts obtained from their mothers in January, 1995.

*Portal vein reconstruction in pediatric liver transplantation from living donors*, Saad, S., Tanaka, K., Inomata, Y., Uamoto, S., Ozaki, N., Okajima, H., Egawa, H., and Yamacka, Y., *Annals of Surgery*, 227(2):275–81 (February 1998), which is hereby incorporated herein in its entirety by reference, discloses that in living related partial liver transplantations, portal vein anastomosis to the confluence, with or without the use of vein grafts, is an optional alternative to end-to-end reconstruction, especially in small children.

*Soluble ICAM-1 (Sicam-1) in congenital biliary atresia*, Minnick, K. E., Kreisberg, R., and Dillon, P. W., *J. of Surgical Research*, 76(1), 53–6 (April 1998), which is hereby incorporated herein in its entirety by reference, discloses that SICAM-1 (Soluble Intercellular Adhesion Molecule-1) is markedly elevated in congenital biliary atresia, reflecting the immunopathology of the disease process, but it does not appear to correlate with markers of liver function. SICAM-1 may be useful in assessing the effects of immunomodulatory therapy.

*Diverse morphology of biliary atresia in an animal model*, Petersen, C., Grasshoff, S., and Luciano, L. *Journal of Hepatology*, 28(4): 603–7 (April 1998), which is hereby incorporated herein in its entirety by reference, discloses diverse morphology of congenital biliary atresia in an animal model and relates the findings to congenital biliary atresia in children. Extrahepatic congenital biliary atresia can be simulated in Balb/c-mice which have been infected with a rotavirus. Irreversible occlusion of the common bile duct is the result of an inflammatory process of the whole biliary tract. The observations in this animal model are analogous to observations of extrahepatic congenital biliary atresia in newborn children. This original model can be used to help determine the minimal therapeutic dose required of the present invention per animal weight of this nutrient therapy (similar concept to toxicologic studies for minimal lethal dosage). These studies suggest that most types of extrahepatic congenital biliary atresia in children can be mimicked in an animal model.

*Neurodevelopmental outcome of young children with extrahepatic congenital biliary atresia 1 year after liver transplantation*, Wayman, K. I., Cox, K. L., and Esquivel, C. O., *Journal of Pediatrics*, 131(6):894–8 (December 1997), which is hereby incorporated herein in its entirety by reference, stresses that urgent nutritional therapy is a preventive measure for development delay.

*A case series of transplant recipients who despite immunosuppression developed inflammatory bowel disease*, Riley, T. R., Schoen, R. E., Lee, R. G., and Rakela, J., *American J. of Gastroenterology*, 92(2):279–82 (February 1997), which is hereby incorporated herein in its entirety by reference, discloses a small number of patients who developed inflammatory bowel disease (IBD), including Crohn's Disease, after solid organ transplantation, one of which had pre-transplantation diagnosis of congenital biliary atresia, despite use of immunosuppressive therapy.

Congenital biliary atresia is similar to infantile asthma; the asthma and associated inflammation and edema occur in the tracheobronchial tree, whereas in congenital biliary atresia, the shock organ and associated inflammation and edema occur in the biliary tree. In a preferred embodiment, the method and composition of the present invention treats congenital biliary atresia without resulting in cirrhosis or inflamatory bowel disease, two common ailments suffered by children having received conventional therapy for congenital biliary atresia.

SUMMARY OF THE INVENTION

The present invention relates to a composition and uses thereof for treatment of damaged tissue comprising at least one essential amino acid in L form and at least one essential lipid; wherein the composition is administered to a mammal suffering from severe tissue damage. The invention further relates to a composition and uses thereof comprising a mixture of one or more free L-amino acids in which the molar ratio of the free L-amino acids corresponds to the molar ratio of amino components in a mammalian tissue protein; and at least one essential lipid.

The invention also relates to a composition comprising a mixture of one or more free L-amino acids and at least one essential lipid; wherein the molar ratio of the free L-amino acids corresponds approximately to the molar ratio of amino components in a medicament, particularly a cyclosporin or penicillin. For example, the activity of cyclosporin or penicillin can be mimicked by administration of a therapeutic formulation having components that could be combined to create a ring, linkage, or other moiety that mimics a lactam ring and more particularly mimic the CO—N bond of the beta-lactam ring, which is believed essential to the therapeutic activity of penicillin and cyclosporin. Furthermore, the inventive therapeutic formulations avoid microorganism metabolites and proteins such as those having D-alanine and D alanyl groups as are present in penicillin. It is believed that by providing the amino acid stereoisomers native to the mammalian body—namely, L amino acids—in optically pure form, regeneration of damaged tissue is enhanced.

DESCRIPTION OF PREFERRED EMBODIMENTS

1. Therapeutic Formulations

Figure 1:
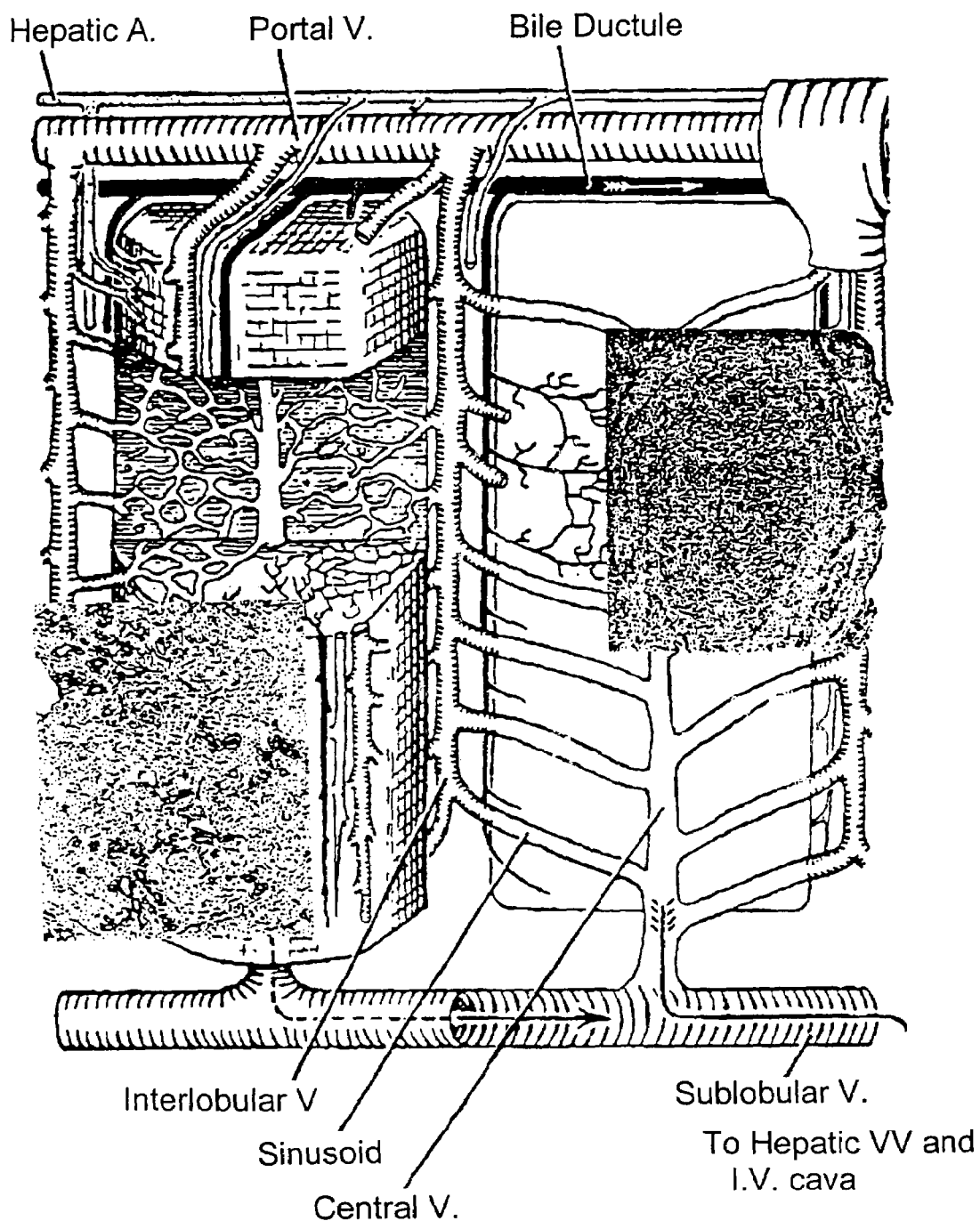
FIG. 1 is a schematic drawing of a liver illustrating the locus of congenital biliary atresia disease being close to the location of stem cells and in approximately the area of believed therapeutic activity. Biliary atresia is evidenced by a sheet of periductular inflammation and fibrosis. Also shown on this H&E slide is extensive periductule inflammation. This inflammatory obstruction also prevents re-anastomosis of the biliary ductules diagrammatically illustrated here by superimposing the histopathology of biliary atresia upon the normal microscopic anatomy of the liver.

The present invention involves administering to a mammal a therapeutic formulation comprising a mixture of at least one free L-amino acid, including at least one free essential amino acids in L stereoisomer form; and one or more essential lipids. Preferably, the L-amino acid profile simulates (1) the amino acid components of the proteins normally present in healthy tissue that is now diseased or is a transplanted tissue; or (2) the amino acid components of a medicament, preferably a medicament that is an polypeptide, peptide, protein, or analog of any of these.

L amino acids are used in the invention because this stereoisomer is what the mammalian body naturally makes and uses. Preferably, the therapeutic formulations of the inventions contain L amino acids in optically pure form. Optically pure is herein defined as having at least 90% by weight of one stereoisomer and 10% by weight or less of one or more other stereoisomers. Preferably the L amino acids are at least 95% by weight of the L isomer and 5% by weight or less of the D isomer, and most preferably over 99% by weight of the L isomer and 1% or less by weight of the D isomer. Optically pure L amino acids are commercially available and also are readily obtainable by methods known to those of skill in the art, for example, by synthesis from an optically pure intermediate.

Essential amino acids are defined as the amino acids that must be supplied in the diet because the organism cannot synthesize sufficient quantities of them. Essential amino acids for adult humans are arginine, histidine, isoleucine, leucine, lysine, methionine, threonine, tryptophan, and valine. Essential amino acids for other groups of patients are known to those of skill in the art. Free amino acids as used herein mean amino acids that are not part of a peptide or a protein. Free amino acids may be in acid or salt form.

Essential lipids are defined as the lipids that must be supplied in the diet because the organism cannot synthesize sufficient quantities of them. For mammals, the essential lipids include linoleic and linolenic acids. The essential lipids are preferably obtained from flaxseed, soy, safflower or sesame oils.

Analog is defined as a chemical component with a structure similar to another but differing from it in respect to a certain component. An analog may have a similar or opposite action metabolically.

One preferred therapeutic composition comprises one or more free essential amino acids in L form, one or more essential lipids, one or more protective antioxidant lipids (such as EPA), and one or more mucopolysaccharides, such as chondroitin sulfate. Another preferred therapeutic composition comprises one or more free essential amino acids in L form, one or more essential lipids, one or more protective antioxidant lipids (such as EPA), one or more phospholipids, and one or more glycolipids. Yet a more preferred embodiment further comprises lipoproteins.

Optionally, the therapeutic formulation may further comprise one or more simple sugars (e.g., monosaccharides or disaccharides), such as glucose or fructose; one or more nonessential fats or lipids such as triglyceride fats, mono- and diglycerides, phospholipids such as phosphatidyl choline and phosphatidyl serine, glycolipids, and lipoproteins; vitamins; minerals; amino acid-like components such as taurine and carnitine; and choline. Preferably, at least one fish oil derived fatty acid lipid or fat, such as EPA (eicosopentanoic acid), and at least one short or medium chain fatty acid lipid or fat (as a source of quick energy rather than fat storage) is also present.

Optionally, at least one mucopolysaccharide such as shark cartilage, chondroitin sulfate, collagen, cartilage, hyaluronic acid and hyaluronan mucopolysaccharide is also present in the therapeutic formulation. The mucopolysaccharide is believed to stimulate the immune system and to have anti-neo-inflammatory and anti-neoangiogenesis activity.

Preferably, the therapeutic compositions comprise amino acids in ratios that correspond generally to the ratios of amino acid components in healthy tissue, embryonic cells, or a medicament.

For example, damaged skin, such as that caused by scurvy, atopic dermatosis, psoriasis, or pemphigus, can be treated by a therapeutic formulation that mimics the amino acid components of healthy skin protein. One example of such a therapeutic formulation is as follows: 3 moles L methionine, 16 moles L proline, 13 moles L tyrosine, 30 moles L asparagine, 8 moles L phenylalanine, 20 moles L cysteine, 50 moles L leucine, 38 moles L serine, 29 moles L arginine, 21 moles L threonine, 21 moles L valine, 3 moles L histidine, 9 moles glycine, 22 moles L alanine, 14 moles L isoleucine, 2 moles L tryptophan, 46 moles L glutamic acid, 12 moles L lysine, 14 moles L aspartic acid, and 32 moles of L glutamine. The molar ratios may vary about 50%, and more preferably about 10%, and still provide the inventive therapy. For example, the 2 moles of L tryptophan in the above formula may be considered 2 plus or minus 1 mole L tryptophan and, more preferably, 2 plus or minus 0.2 mole L tryptophan. To treat scurvy, the above formulation would be administered either orally or topically in combination with 500 to 1000 milligram ascorbic acid daily. Scurvy is known to result in skin at the edge of wounds that has an almost complete absence of the 3 and 4 hydroxy proline of hydroxylated L proline amino acids normally present as 16 of the 404 moles in the amino acid components of skin protein. It is believed that the formulation of the invention will work by providing a complete replacement amino acid mixture to allow formation of new, complete skin protein that will accelerate the healing resulting from ascorbic acid therapy.

Another example is a formulation that mimics the amino acid components of fibrinogen. The deficiency of fibrinogen called a fibrinogenemia or hypofibrinogenemia can result in blood clotting deficiencies (abnormal hemostatis), a coagulopathy. In addition to the common therapy of intravenously administering the sterile fraction of normal fibrinogen found in human plasma, the following inventive therapeutic formulation can be administered orally to accelerate improvement of clotting: 15 moles L methionine, 41 moles L proline, 24 moles L tyrosine, 30 moles L asparagine, 28 moles L phenylalanine, 13 moles L cysteine, 51 moles L leucine, 107 moles L serine, 54 moles L arginine, 59 moles L threonine, 45 moles L valine, 19 moles L histidine, 97 moles glycine, 37 moles L alanine, 26 moles L isoleucine, 19 moles L tryptophan, 64 moles L glutamic acid, 42 moles L lysine, 50 moles L aspartic acid, and 30 moles L glutamine. The molar ratios may vary about 50%, and more preferably about 10%, and still provide the inventive therapy. By coadministration of this inventive formulation with administration of normal fibrinogen, the dependency on intravenous medication is reduced.

Without being limited by theory, it is believed that the inventive therapeutic formulations work to promote tissue repair by providing stem cells with the optimal ratios and proper stereoisomer form of amino acids that are needed to synthesize new tissue or to allow the synthesis in vivo of a desired medicament. Furthermore, it is believed that by supplying the body with the chemical components of the extracellular matrix, such as cartilage-containing chondroitin sulfate and collagen, tissue repair and antiinflammatory anti-neoangiogenesis is enhanced. Also, it is believed that the two essential fatty acids, linolenic and linoleic acids, and eicosapentanoic acid (EPA) favorably enhance the body's production of anti-inflammatory prostaglandin 3 and prostaglandin 1 over the production of prostaglandin 2, which has been shown to mediate disease. Cell membrane formation and repair is believed enhanced synergistically by the administration simultaneously (as in one formulation) of lipids, phospholipids, lipoproteins essential fatty acids, and EPA.

Without being limited by theory, it is believed that the present invention functions by the method of altering the balance of free L amino acids such that under the law of mass action, protein synthesis is favored over proteolysis. By adding additional free amino acids, the activity of enzymes involved in protein synthesis and degradation, such as proteases, is driven in the direction of protein synthesis and therefore in the direction of tissue production rather than protein degradation. Also, it is believed that the addition of L amino acids inhibits or arrests the catabolic the protein degradation reactions of these enzymes.

It is believed that the therapeutic compositions of the present invention can be used to achieve similar therapeutic effect as cyclosporins. Cyclosporins are a group of nonpolar cyclic oligopeptides with immunosuppressant activity. The therapeutic formulations of the invention would be advantageous over cyclosporin because it is believed that the inventive compositions would not have any of the following risks associated with cyclosporin therapy: cancer, nephrotoxicity, and hepatotoxicity. Cyclosporin effects are expected with the following composition (composition no. 1): 2 moles L valine, 4 moles L leucine, 2 moles L alanine, 1 mole glycine, and 2 moles of a methyl donor, such as methionine or betaine. The molar ratios may vary about 50%, and more preferably about 10%, and still provide the inventive therapy. For example, the 2 moles of L valine in the above formula may be considered 2 plus or minus 1 mole L valine and, more preferably, 2 plus or minus 0.2 mole L valine. Optionally, one mole of a methyl donor such as methionine or betaine is substituted with 1 mole of gamma amino butyric acid, also called 4-amino butyric acid (composition no. 2). Another preferred embodiment has the same components as composition no. 1 or no. 2 and further comprises one mole of a nine carbon ring amino acid derived from the metabolism of a microorganism such as the fungus Tolypocladium inflatum Gams, and an additional mole of a methyl donor. The molar ratios may vary about 50%, and more preferably about 10%, and still provide the inventive therapy.

Preferably, the therapeutic formulation administered to mimic the effects of cyclosporin is comprised of optically pure L stereoisomers of the desired amino acids. If a formulation of optically pure L stereoisomers fails to yield the desired results in an acceptable time frame, however, it may be desirable to substitute 1 molar ratio of alanine in an optically pure D form for the L form. Such a substitution should more closely resemble the stereochemistry of the amino components naturally found in cyclosporin.

Although sulfasalazine (also known as azulfidine) is not a protein or peptide, it is believed that the therapeutic effects of sulfasalazine can be mimicked by a therapeutic formulation of the present invention in which the presence of four nitrogen linkages, such as are present in sulfasalazine, may be simulated by an electron affinity of three or more high energy amphoteric, zwitterionic essential and non-essential L amino acids, preferably amino acids having aromatic side chains such as phenylalanine, tyrosine, and tryptophan. Alternately, if the desired therapeutic goals are not achieved in an acceptable time, one mole of 5 aminosalicylate may be substituted for one of the three moles of high energy amino acids specified above. This internal milieu equilibrium might also be aided by bonded van der Waals forces, as is believed to function in the inventive therapeutic formulation corresponding to cyclosporin.

It is also believed that the therapeutic effects of protease inhibitors can be mimicked by a therapeutic formulation according to the present invention.

It is also believed that the therapeutic effects of antibiotics such as penicillin and cephalosporin can be mimicked by a therapeutic formulation of the present invention comprising amino acids that correspond to the amino components in a lactam ring, and particularly that correspond to the components in the CO—N bond of the beta-lactam ring. For example, a formulation comprising L alanine may be used. Also, a formulation of L glutamic acid may be used, as glutamic acid may lose one mole of water during digestion and metabolism to form a lactam of glutamic acid.

The therapeutic formulations of the present invention work with negligible risk of side effects or complications from therapy and are very safe.

2. Formulations and Dosaging

The flavoring of the inventive therapy is a concern when not used in infancy. The free amino acids have a very disagreeable flavor that must be masked to obtain good patient compliance with the therapy. Oral formulations having elemental amino acids that are intended for patients over the age of one year preferably include one or more flavorants, synthetic or natural, such as grape, grapefruit, especially pink grapefruit, vanilla, cream, apple, chocolate (especially hypoallergenic). Milk permeates (especially hypoallergenic milk permeates) may be used, but preferably the microorganism debris is minimal. Most preferably no microorganism debris is detectable in milk permeates used as flavorants.

Optimal efficacy of the inventive formulations and therapy occurs with concurrent avoidance of foods having exogenous catabolic debris, such as foods containing microorganism flora, debris and protein products, and avoidance of foods that have been pasteurized, such as pasteurized dairy products. Foods to avoid include those of such potentially significant microorganism content that pasteurization is required and foods prepared by enzymatic activity of microorganisms, such as cheeses and wines produced by fermentation. The avoidance of foods with exogenous microorganism catabolic debris is believed to minimize or reduce the competition between catabolic products and the nutrients of the present invention and thereby drive protease activity that favors formation of healthy tissue and organ repair. The microorganism catabolic products, including lipopolysaccharide (LPS), and especially microorganism protein LPS, are expected to oppose the desired protein synthesis. Additionally, toxic metabolites of Aspergillus such as are found in peanuts are preferably avoided. In particular, patients suffering with Crohn's disease (regional ileitis) and congenital biliary atresia should avoid milk products. Preferably, the therapeutic formulation is free of hydrocolloids, preferably the hydrocolloids that might cause gastrointestinal irritation and inflammation.

This invention is applicable to treatment of all age groups, including prenatal, pediatric, adult and elderly. The invention is envisioned for use in treating any mammal. For example, the inventive therapy may be used to prevent or slow the cyclic epidemic spread of Johne's Disease (ileitis) in dairy cattle and other similar animals.

Proper dosages can be ascertained by one of skill in the art using the teachings of this disclosure and readily available literature. Free amino acids may be derived from natural sources or synthetically produced. Suppliers include Ajinomoto USA of Torrance, Calif. and Tanabe USA Inc. of San Diego, Calif. One preferred source of amino acids is Neocate® elemental diet, sold by SHS of Liverpool, UK, which contains inter alia essential and non-essential amino acids, dried glucose syrup, fat, minerals, trace elements and vitamins.

The preferred amino acid dosages of the inventive therapeutic formulations are below the dosages recommended for an elemental diet for infants or others having gastrointestinal problems. Preferably, total daily free amino acid dosage is less than 20 grams, more preferably less than 15 grams, and still more preferably less than 10 grams. A preferred regime comprises administering 1–2 grams free amino acids three to four times daily, for a total dosage of three to eight grams daily. The higher dosages needed for a complete dietary supplement are commonly rejected by all but infants under age one because of the unpleasant taste and smell of free amino acids. By using much lower dosages, the present invention promotes patient compliance because small dosages may be administered in capsules or with flavorings such that taste problems are minimal.

Dosaging is dependent upon the age, body weight, and medical condition of the patient. Because of the negligible risks associated with the inventive therapy, higher dosages may be considered in more critical cases. The preferred effective total daily dosages of free amino acids is 0.5 to 20 grams, and more preferably 1 to 10 grams per day for an adult. One half that dose is appropriate for children age six to twelve, and one-quarter that dose for children under age six. Preferably the daily dosage is divided into 3 to 6 administrations per day.

Preferably, the amino acids are provided in total daily dosages that are within the following weight ranges:

L alanine preferred dosage, 0.05–12.5 grams, more preferred dosage, 5–9 grams.

L arginine preferred dosage, 0.05–12.5 grams, more preferred dosage, 1–9 grams.

L asparagine preferred dosage, 0.05–12.5 grams, more preferred dosage, 0.5–9 grams.

L aspartic acid preferred dosage, 0.05–6 grams, more preferred dosage, 0.5–6 grams.

L cysteine preferred dosage, 0.1–1 gram, more preferred dosage, 0.5–1 grams.

L cystine preferred dosage, 0.5–12.5 grams, more preferred dosage, 0.5–9 grams.

L glutamine preferred dosage, 0.5–12.5 grams, more preferred dosage, 0.5–9 grams.

L glutamic acid preferred dosage, 0.5–<6 grams, more preferred dosage, 0.5–6 grams.

Glycine preferred dosage, 0.5–12.5 grams, more preferred dosage, 0.5–9 grams.

L histidine preferred dosage, 0.5–12.5 grams, more preferred dosage, 0.5–9 grams.

L isoleucine preferred dosage, 0.5–12.5 grams, more preferred dosage, 1–9 grams.

L leucine preferred dosage, 0.5–12.5 grams, more preferred dosage, 0.5–5 grams.

L lysine preferred dosage, 0.5–12.5 grams, more preferred dosage, 0.5–9 grams.

L methionine preferred dosage, 0.5–12.5 grains, more preferred dosage, 0.0.5–9 grams.

L phenylalanine preferred dosage, 0.5–12.5 grams, more preferred dosage, 0.5–9 grams.

L proline preferred dosage, 0.5–12.5 grams, more preferred dosage, 1–9 grams.

L serine preferred dosage, 0.5–>6 grams, more preferred dosage, 0.5–6 grams.

L threonine preferred dosage, 5–12.5 grams, more preferred dosage, 0.5–9 grams.

L tryptophan preferred dosage, 0.5–>6 grams, more preferred dosage, 0.5–6 grams.

L tyrosine preferred dosage, 0.5–12.5 grams, more preferred dosage, 0.5–9 grams.

L valine preferred dosage, 0.5–5 grams, more preferred dosage, 0.5–9 grams.

L taurine preferred dosage, 0.5–12.5 grams, more preferred dosage, 0.5–9 grams.

L carnitine preferred dosage, 0.5–12.5 grams, more preferred dosage, 0.5–9 grams.

The relative ratios of amino acids are derived as disclosed earlier from the ratios present in healthy tissue or medicament. These preferred molar ratios are then used to make a formulation for maximal dosage in 390 mg to 500 mg capsules administered as about 5 capsules three to four times daily preferably. The total weight of an individual amino acid preferably should fall within the preferred weight ranges provided above.

The amino acids administered orally are readily available for absorption in the GI tract with minimal if any degradation or processing required in the GI tract. This conserves the energy required by the GI tract and the spare energy can be used to repair diseased tissue or damaged organs.

This non-invasive medical therapy may be utilized with patients waiting for an organ transplant, or if possible, at an earlier stage in the organ disease. For example, the therapy may be administered prenatally by the mother ingesting the therapeutic formulations or by direct administration of the formulation to the fetus.

Duration of the inventive therapy is from a few weeks to several months. Longer duration of therapy may be considered because of the negligible risks associated with the inventive therapy.

The compositions of the present invention may be formulated for oral, topical or parenteral use, especially oral. The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation. Oral liquid preparations are typically in the form of a dry powder for reconstitution with water or other suitable vehicle before use. For parenteral administration, fluid unit dosage forms are prepared utilizing the therapeutic formulations of the invention and a sterile vehicle, water being preferred. It is also possible to prepare an oral mucosal delivery system such as that described in U.S. patent application Ser. No. 09/080,990, entitled "Methods and Compositions for Oral Delivery of Vitamins, Minerals, and Medications", which is incorporated in its entirety herein by reference.

In special indications, particular precautions are necessary. For example, with a patient having a coma or near coma with high ammonia levels, such as a patient suffering a complication of alcoholic cirrhosis, several L amino acids, such as L glutamate (also called L glutamic acid), and L aspartic acid, are desirable because they are believed to aid in ammonia removal. L glutamine is preferably avoided with cirrhosis of the liver, kidney disease, Reye's syndrome, or any other disease with increased ammonia blood levels. L cysteine, for a patient having a chronic illness, may be required at a level of 1 gram three times daily for one month. L arginine should be avoided during pregnancy and breast feeding. In patients with schizophrenia, L arginine is preferably administered at dosages of less than 30 milligram per day.

L valine, L isoleucine and L leucine each have branched aliphatic side chains. These amino acids are very helpful in diseases resulting from aging, as well as for trauma and infection. L tyrosine, L tryptophane, L phenylalanine and L histidine are advantageous for elderly patients with neurologic problems and depression. L methionine and L taurine are preferably used in hypersensitivity and autoimmune diseases.

Additionally, useful therapeutic applications for specific amino acids are provided in Table 1. This additional information may be useful in identifying specific cell or tissue proteins whose amino acid components can be mimicked in a therapeutic formulation of the invention. For example, tissues can be analyzed to locate high concentrations of specific amino acids known to favorably treat a specific ailment. From these tissues, specific proteins can be identified that are related to the ailment and the amino components of these proteins can be administered in one of the therapeutic formulations of the invention.

TABLE I

| Amino Acids | Tissue Healing | Immune System Antibody (Ab) Formation | Cell Function DNA RNA Genetics | Skin Texture | Cancer | AIDS | Drug Addiction Amino Acid Deficiency | CNS | Neuro Transmitte | Antiaging Anabolic Growth |
|---|---|---|---|---|---|---|---|---|---|---|
| L Lysine | ++ | +Ab | | | | | | | | ++ |
| L Glutamate | | | | | | | | | | ++ |
| L Leucine | ++ | | | + | | | | | + | +++ |
| L Proline | + | | | + | | | | | | ++ |
| L Arginine | | +Ab | | | | | | | | |
| | +++ | +Immune System | | ++ | + | + | | | | +++ |
| L Valine | ++ | | | | | | | + | | ++ |
| L Isoleucine | ++ | | | | | | | + | | ++ |
| L Aspartic Acid | | +Ab | + | | | | | | | |
| | | +Immune System | sprouts seeds | | | | | + | | ++ |
| L Asparagine | | | | | | | | + | + | |
| L Glycine | + | | + | + | | | | + | | ++ |
| L Threonine | + | +Immune System | | + | | | | | | ++ |
| L Tyrosine | + | | | | | | + | | | + |
| L Phenylalanine | | | | | | | | ++ | + | ++ |
| L Serine | | +Ab | | | | | | | | |
| | | +Immune System | | + | | + | | ++ | | +++ |
| L Histidine | +++ | | + | | | + | | + | | +++ |
| L Alanine | | | | | | | | ++ | | |
| L Tryptophan | | | | | | | | + | + | +++ |
| L Methionine | | ++ | + | + | | | | ++ | | ++ |
| L Glutamine | + | | | | + | | | + | | ++ |
| Taurine | | ++ | + | | | | | | | ++ |
| L Carnitine | | | | | | | | | | + |
| L Cystine | + | | + | + | | | | + | | + |
| L Cysteine | + | | | + | | | | | | + |

| Amino Acids | Liver | Ammonia-Removal & Toxins | G. I. Inflammatory Bowel Disease | Sports Muscle Fatigue Anti-Fatigue | Heart & Cardio-Vascular | Red Blood Cells | Endocrine Hormone | Enzyme Production |
|---|---|---|---|---|---|---|---|---|
| L Lysine | | | | + | | | + | + |
| L Glutamate | + | + | | | | | | |
| L Leucine | | + | | ++ | | | + | |
| L Proline | | | | + | + | | | |
| L Arginine | + | | | | | | + | + |
| L Valine | | | | ++ | | | | |
| L Isoleucine | | | | ++ | | + | | |

TABLE I-continued

| Amino Acids | | | | | | | |
|---|---|---|---|---|---|---|---|
| L Aspartic Acid | + | + | | + | | | |
| L Asparagine | | | | | | | |
| L Glycine | | | | + | | | |
| L Threonine | + | | | + | | | |
| L Tyrosine | | | | | | | + |
| L Phenylalanine | | | | | | | |
| L Serine | | | | + | | | |
| L Histidine | | | | | | | |
| L Alanine | | | | | | | |
| L Tryptophan | | | | | | + | + |
| L Methionine | + | | | + | | + | |
| L Glutamine | + | | + | + | | | |
| Taurine | | | | + | | + | |
| L Carnitine | + | | | + | | | |
| L Cystine | + | | | + | | | |
| L Cysteine | | | | | | | |

| Amino Acids | Arthritis Control | Storage (Fat) | The Control of Blood Sugar | Protein Synthesis | Pos. Nitrogen Balance | Toxic Compounds | Assoc.iated/ Interr-Related Vitamin Use | Radiation Damage Protection |
|---|---|---|---|---|---|---|---|---|
| L Lysine | | + | | + | + | | | |
| L Glutamate | | | + | | | | | |
| L Leucine | | | | | | | + | |
| L Proline | + | | | | | | | |
| L Arginine | + | + | | + | ++ | | | |
| L Valine | | | + | | ++ | | | |
| L Isoleucine | | + | | | | | | |
| L Aspartic Acid | | | | | | | | |
| L Asparagine | | | | | | | | |
| L Glycine | | | | | | | | |
| L Threonine | | | + | | | | | |
| L Tyrosine | | | | | | | | |
| L Phenylalanine | + | | | | | | | |
| L Serine | | + | | | ++ | | | |
| L Histidine | + | | | | ++ | + | + | |
| L Alanine | | | + | | | | | |
| L Tryptophan | | | | | ++ | | | |
| L Methionine | | + | | | | + | | |
| L Glutamine | + | | + | | | | + | |
| Taurine | | + | + | | | | | |
| L Carnitine | | + | + | | | | | |
| L Cystine | | | | | | | + | |
| L Cysteine | | | | | | | + | + |

To protect unstable oils, storage in a frozen or refrigerated final product and/or a dark glass container is desirable to prevent lipid oxidation by light.

Linolenic acid, an omega 3 seed oil most abundant in flaxseed oil, is preferably administered at about 0.5 to 35 grams daily, and more preferably at about 3 to 10 grams daily. The following other lipids preferably are included in the therapeutic formulations of the invention at a preferred dose of 0.25 to 35 grams per day, and more preferably 0.5 to 2.0 grams per day: phospholipids and their essential fatty acids such as compound lipids, glycolipids, mono- and diglycerides, lipoproteins, including, but not limited to, cerebrocides and cephalin, 1 μL lipoproteins such as, but not limited to, lipovitellin, and phosphoproteins. Vitellin is particularly preferred for a fetus at a preferred dosage of 0.5 to 2 grams.

Where shark cartilage is used, an adult dosage is in the range of a dosage of about 740 mg to about 1480 mg administered once to three times daily and preferably 2220 mg administered once daily. For major flare-ups of autoimmune diseases or bronchitis, dosages of up to about 2240 mg three times daily are recommended. Shark cartilage is preferably administered in powder in a capsule and contains cartilage with 12% chondroitin sulfate and collagen. Shark cartilage is sold under the name of Cartilade from BioThera-pies, Inc., Fairfield N.J. When hyaluronic acid and hyaluronan mucopolysaccharides are used, the source may be human umbilical cord tissue. The shark cartilage is immunologically preferred. This species is uniquely not affected by cancer and its skeletal structure is entirely cartilage.

Autologous cartilage and chondrocytes are preferred for patients with arthritis. Preferred amino acid formulations for arthritic patients include the L amino acids combining with the body's glucose to form glucosamine, which is believed to be incorporated into the body's mucopolysaccharides. Such patients also benefit from hyaluronic acid, chondroitin sulfate, shark cartilage and nutrient substrate cartilage, available from many animals including cow, pig and chicken.

The preferred dosage of glucosamine is about 0.5 grams to about 1 gram, 3 times daily. The preferred dosage of chondroitin sulfate is about 250 to about 500 milligrams, 3 to 4 times daily. More preferred is 390 milligrams to 500 milligrams chondroitin sulfate administered three to four times daily. Preferably, chondroitin sulfate is administered in capsule form to minimize any unpleasant taste sensations and thereby encourage patient compliance.

When EPA (eicosopentanoic acid) is used, the dosages may be about 0.36 to about 4.5 g daily, preferably about 0.36 grams to about 0.72 grams daily to three times daily. EPA is readily available commercially in soft gel capsules having 0.36 g EPA and 0.24 g DHA docosahexanoic acid in a 2 gram total fish oil capsule.

Preferably, the medium chain fatty acids used in the therapeutic formulations are triglycerides or other naturally occurring fatty acids found in vegetable oils such as coconut and soybean oils. Medium and short chain fatty acids are desirable because they are readily metabolized to energy, required for acute illness, rather than stored as fat and do not require much processing by liver. Short chain fatty acids, such as but not limited to $C_4$ butyric acid, are also useful in the invention, particularly those present or isolated from hypoallergenic butter.

Such short chain fatty acids have local antiinflammatory action to help treat ileitis or skin burns, preferably in combination with 200 to 400 IU vitamin E oil.

Sugars useful in the present invention, such as glucose, corn syrup solids, and fructose, are preferably administered at the dosages recommended by dietary organizations, and are known to those of skill in the art.

Preferably vitamins and minerals are administered with the therapeutic formulations of the invention. The preferred amounts of these components are provided in Table 2.

TABLE 2

| Daily Adult Vitamins | Where Applicable Dosages | |
|---|---|---|
| Vitamin A | 1000 to 5000 | 5000 to 10,000 IU |
| Beta-carotene | Preferred since 10,000 IU converted to Vitamin A. As needed by the body. | 10,000 to 15,000 IU |
| Vitamin $B_1$ (thiamine) | | 50 mg |
| Vitamin $B_2$ (aribioflavin) | | 50 mg |
| Vitamin $B_3$ | | |
| (niacin) | | 100 mg |
| (niacinaminde) | | 100 mg |
| Pantothenic acid (vitamin $B_5$) | | 100 mg |
| Vitamin $B_6$ (pyridoxine) | | 50 mg |
| Vitamin $B_{12}$ | | 300 mcg |
| Biotin | | 300 mcg |
| Choline (also in phospholipids such as P.C. phosphotidyl choline) | | 100 mg |
| Folic acid | | 800 mcg |
| Inositol | | 100 mg |
| Para-aminobenzoic acid (PABA) | | 50 mg |
| Vitamin C | (optional preferred with mineral ascorbates) 50 mg to 250 mg | 50 mg to 3,000 mg |
| Bioflavonoids (mixed) | | 500 mg |
| Hesperidin | | 100 mg |
| Rutin | | 25 mg |
| Vitamin D | | 400 IU |
| Vitamin E | 200 to 400 IU | 600 IU |
| Vitamin K (use natural sources such as alfalfa, green leafy vegetables) | | 100 mcg |
| Calcium | 800 mg to 1000 mg | 1,000 mg 1,500 mg (pregnancy & post menopausal) |
| Chromium(GTF) | | 150 mcg |
| Copper | | 3 mg |
| Iodine (kelp is a good source) | | 225 mcg |
| Iron | | 18 mg |
| Magnesium | | 750–1,000 mg |
| Manganese | | 10 mg |
| Molybdenum | | 30 mcg |

TABLE 2-continued

| Daily Adult Vitamins | Where Applicable Dosages |
|---|---|
| Potassium | 99 mg |
| Selenium | 200 mg |
| Zinc | 50 mg |

3. Uses of the Invention

The present invention is particularly effective for treating congenital biliary atresia. Congenital biliary atresia is a stem cell focused disease. A small population of stem cells located in the junction between liver cells and the smallest segments of the biliary tree (as shown in FIG. 1) may differentiate into liver cells and biliary dust epithelium and are known to participate in regeneration that occurs in certain forms of hepatitis. Thus, in congenital biliary atresia the stem cells are able to grow new tissue and are located in close proximity to the damaged tissue. The damaged tissue as shown in FIG. 1 has periductular inflammation and fibrosis. The locus of maximal disease is at the junction of the smallest ductules of the biliary tree and the adjacent liver cells (hepatocytes), which is also the location of stem cells that are capable of regenerating liver tissue cells.

The invention is also effective for treating bronchial asthma. Without being bound by any theory, that disease is believed to be similar to congenital biliary atresia, because it results in inflammation or blockage of small tubules that probably are in close proximity to stem cells. In bronchial asthma, the blockage occurs in very small tubules or bronchioles, which are unprotected by the support of cartilage in contrast to the remainder of the bronchial tree.

Dramatic relief from asthma symptoms has been observed in asthmatic patients, usually young children, that are receiving elemental feedings as complete nutritional support because of cow milk allergies. Furthermore, such patients have not been observed to suffer from "dismodeling", a term used herein as a synonym for remodeling, and such patients are able to discontinue or reduce the use of inhalation therapy of corticosteroids and bronchodilators.

The therapeutic compositions according to the present invention should help reduce the risks of adverse reactions associated with the use of certain allergenic plasticizers in renal dialysis, and thereby prevent recurrent anaphylaxis in dialysis and ameliorate acute flareups. Furthermore, the therapeutic compositions are believed useful in reducing the risk of kidney transplantation rejections.

Without being bound to any theory, it is thought that the essential components of the therapeutic formulations promote favorable substrate nutrition in vivo as well as in vitro for stem cells to thrive in tissue repair, replacement and regeneration. Such effects are believed to occur in mesodermal and mesenchymal tissue as well as endodermal surfaces, such as the respiratory tract. Asthma may be treated. Ailments of the GI tract such as regional ileitis (Crohn's Disease), and other inflammatory bowel diseases, including ulcerative colitis, mucous colitis, and liver disease such as, but not limited to, congenital biliary atresia, are all believed to be amenable to treatment with the inventive formulations and therapy. The inventive therapy is particularly advantageous for inflammatory bowel diseases that are very resistant to present therapies.

Furthermore, the simultaneous administration of components of the therapeutic formulations is believed to work synergistically to promote tissue healing at higher levels and at a more rapid speed than if the components were administered individually at different times. In particular, the administration of a combination of L-amino acids is believed to be much more effective therapy than administration of the same amounts of individual amino acids over time such that the individual amino acids are not concurrently in the blood stream.

The inventive non-invasive therapy can be used also in the treatment of deforming diseases, such as leprosy, and skin and nerve damage. Bacterial infections and epidemics, such as drug resistant tuberculosis epidemics, may also be treated with a therapeutic formulation in which the components mimic the components of an antibiotic.

Diseases of the ectodermal surfaces including skin, hair, nails and teeth, are amenable to amelioration by use of the inventive compositions and therapy. In particular, eczema, urticaria and psoriasis may be treated. The therapeutic formulations according to the present invention can accelerate healing and reduce the risks of corneal graft rejection.

Diseases akin to congenital biliary atresia from a therapeutic standpoint (e.g., ileitis) will show dramatic results from the present invention. For example, a patient having ileitis will not require corticosteroids for as long as seven months after therapy with a therapeutic formulation has been administered successfully and discontinued.

In the aging process, when the production of digestive enzymes and growth hormone is diminished, the free amino acids of the inventive non-invasive therapeutic composition are anabolic and stimulate production of growth hormones, both of which are beneficial.

The inventive therapeutic formulations of the present invention may be used to drive anabolic processes for immunopathies such as milk allergies, colitis, and autoimmune diseases.

Furthermore, it is believed that the therapeutic formulations of the present invention can be used with AIDS patients on antiprotease drugs as a substrate analog and metabolic analog. Without limiting the invention in any way, it is believed that by administering the therapeutic formulations of the present invention and avoiding or minimizing ingestion of foods containing protein or peptides or containing microorganism metabolites or catabolic products (such as dairy products), the patient's recovery is enhanced for the following reasons. The gastrointestinal (GI) tract will be only minimally occupied in proteolysis of exogenous proteins and will still serve its immune-like functions, such as control microorganisms (an antibiotic-like function), fight viruses, and aid in the repair of injured tissue to permit tissue healing. AIDS patients on conventional anti-protease drugs often have extreme hyperlipidemia, with serum triglyceride levels of 3,000 to 6,000 mg %. The conventional anti-protease medication may need to be withdrawn to protect the heart and blood vessels from the medication's side-effects, such as coronary artery disease. Administration of the therapeutic formulations of the present invention to AIDS patients on antiprotease drugs with concurrent avoidance of ingestion of the foods described above is expected to solve this dilemma and reduce the undesirable side effects of the drugs because the GI tract will only be minimally involved in protein breakdown or proteolytic action. It is believed that the proteases throughout the body will be coerced by the law of mass action into cell and tissue anabolism.

It is further believed that the therapeutic formulations of the invention can be used as a supplement to antiprotease therapy, and thereby to allow for antiprotease dosages to be lessened and thereby their side effects reduced while achieving the same therapeutic results. Preferably, AIDS patients on the inventive therapy avoid ingesting catabolic products of microorganisms including their metabolites such as bacterial proteins and their metabolites, including dairy products and cheeses. Furthermore, it is believed that the inventive formulations will act to repair HIV-damaged cells and tissue by supplying the building blocks needed, namely, amino acids, cell wall components, and extracellular matrix components. Furthermore, by the administration of these building blocks together in one formulation, it is believed that the components will act synergistically to allow for much faster and more complete cell and tissue repair than if administered separately. Without intending to limit the invention in any way, it is believed that the law of mass action will apply to cause proteases throughout the body to act to create proteins rather than degrade them.

4. Individualized Therapy

To optimize therapy with the present invention, an individual profile of each patient is compiled and stored. Information collected includes blood protein types, lipid levels, DNA sequence, nutrient component levels in the blood including the amino acid composition, and nutrient levels in the cells, tissue and organs. In particular, amino acid composition of organs and tissues is collected. This information may be used to individually design a therapeutic formulation, which includes the L amino acids in molar ratios dictated by the cell and tissue analyses. Furthermore, blood and tissue samples may be stored for future comparative reference.

It would be advantageous to employ computer software that could help identify preferred therapeutic formulation components and their molar ratios based upon a comparison of formulations administered to patients having similar profiles. Also, computer software could be designed to compare the chemical components of particular ribosomes or tissues with the structures of L-amino acids and provide an amino acid formulation that corresponds to the chemical components in their correct molar ratios in a particular ribosome. Ribosomes are the organelles of protein synthesis.

Diseased tissue may be chemically analyzed and compared with healthy adjacent tissue to determine the nutrients needed using specially designed software. Nutrient-specific stains such as Coommassie Blue may be employed to identify amino acids, proteins and other nutrients in tissue samples. MRI spectroscopic analysis and other analyses known to those of skill in the art may be used to determine tissue and cell chemical composition and thereby discover the deficient nutrients.

It is also envisioned that a medical professional will track the success of the therapy by measuring the chemical components, including the nutrients, in the damaged or replaced tissue during the period of therapy. Such measurements may be made by the invasive practice of tissue biopsy. Preferably when biopsy tissue is removed for diagnosis for another aspect of the patient's therapy, some tissue cells will be used for a nutrient composition analysis. For example, some patients suffering from Crohn's disease have tissue removed for diagnostic purposes. Such tissue could also be used for a nutrient composition biopsy (with molar ratios). Also, non-invasive methods of measuring tissue or cell composition, such as MRI spectroscopic analysis, blood analysis, analysis of secreted liquids, and other analyses known to those of skill in the art may be used.

5. Diagnostic Methods for Milk Allergies

The present invention concerns also a novel method and device for diagnosing milk allergies. It has commonly been supposed that milk proteins and milk sugars are responsible for milk allergies. The diagnostic methods of the present invention are believed new because they are based upon the belief that the principal allergens in dairy products are not milk proteins and milk sugars but rather are the metabolic and catabolic products of bacterial activity and of viral activity, and also bacterial and viral proteins resulting from bacteria, mold and viruses present in dairy products. Thus, testing for allergic responses to bacterial and viral proteins and by-products is appropriate to diagnose and treat milk allergies. Accurate testing for milk allergies would be very useful to allow correct diagnosis and proper treatment of these allergies.

Without limiting the invention, it is believed that microorganism, including bacterial and mold, and viral proteins rather than milk proteins and sugars give rise to milk allergies for the following reasons. First, milk allergies currently are associated with almost 100% negative skin tests when the protein fraction of milk is used as the suspected allergen. It is believed that the carbohydrate and lactose fraction of milk harbors microbial agents and, therefore, this fraction should be tested to diagnose milk allergies. Second, although lactase when added to milk provides a milk that does not give rise to allergic responses in many patients, the lactase used commercially is present with unnamed proteases that degrade allergenic microbiologic and viral proteins. Thus, the success of lactase-fortified milk products may be due to degrading microbial and viral protein products rather than degrading milk proteins and milk sugars.

Without limiting the scope of the invention, it is believed that the catabolic and metabolic products of bacterial and viral activity function in at least two ways in the mammalian body. First, such products are believed to drive protease activity in the direction of protein degradation under the law of mass action. Second, such products operate as allergens in sensitive patients. By avoiding foods containing these products, allergies, particularly milk allergies, are treated and allergic symptoms are reduced.

To aid these goals, allergies, particularly milk allergies, can be diagnosed by testing for allergic responses to bacterial and viral proteins, and to catabolic and metabolic products of bacterial and viral activity. In particular, it is believed that by testing for response to bacterial lipopolysaccharides ("LPS"), many milk allergies may be diagnosed. Other possible allergens are proteins produced by rotavirus and avian or bovine tuberculosis.

The physical methods of immunological testing are well known to those of skill in the art. For example, an immediate allergic response can be shown in a positive result to a skin test. If a skin test does not show a response, then it may be advisable to inject the skin intradermally to determine if a response occurs. A delayed response may be shown several ways. For example, the patient may notice a response to a skin test 48 to 72 hours after the skin test is administered. Also, the patient may notice coughing or wheezing, or have great intestinal distress, 48 to 72 hours after a suspected allergen is contacted with the patient's skin.

More particularly, allergens may be identified by using one of the following diagnostic tests. To test for hypersensitivity to viral proteins and the products produced by viral activity, including rotavirus antigen hypersensitivity, an extract is prepared from the extraembryonic fluid of a chicken embryo infected with the virus. The extract is concentrated and purified by differential centrifugation. The virus is killed with formaldehyde solution 1:1000 and is diluted with isotonic sodium chloride solution. The resulting product contains approximately 0.012 moles glycine and less than 1:8000 formaldehyde solution. Thimerosal is added as a preservative 1:10,000. Each ml of the skin test antigen contains 40 complement-fixing units. After shaking, the product is slightly opalescent. The product is administered first as a skin test. If the patient shows no response, the product is administered intradermally in 0.05 cc and then 0.1 cc dosage if 0.05 cc intradermally is negative. The test, like a tuberculin test, is read 48 to 72 hours after contact with the suspected allergen. The test is also read immediately after the scratch test and 10 to 15 minutes after the intradermal test.

A test for bacterial hypersensitivity may be performed similarly to the example provided for viral hypersensitivity and according to standard methods of making and administering bacterial vaccines and allergenic extracts known to those of skill in the art. Such tests preferably include analyses of hypersensitivity to bacteria common in dairy products and their flora, catabolic, and metabolic products. Tests for hypersensitivity to molds found in milk products may be performed using methods similar to those disclosed herein for allergenic extracts and the knowledge of one with skill in the art.

These microorganism agents in milk allergy are believed to include debris of microorganisms killed by pasteurization, which maintain allergenicity even after the microorganism is no longer infectious. Preferably immunological testing for milk allergies includes testing for these agents.

It is well known that dairy cattle are exposed to viruses and bacteria, sometimes at high levels, which would give rise to the appearance of viral and bacterial allergens in milk. For example, British dairy scientists found paratuberculosis spread quickly through water ponds where fecal paratuberculosis ileitis was present. The spread of this disease was limited by using drinking troughs and by raising the pasteurization temperature 3° C. to 75° C., from 72° C.

As confirmation of the present theory, it is noted that sheep, whose meat and milk products are much less allergenic than beef and cow milk products, have a low incidence of paratuberculosis. The incidence is as low as 1% in diary sheep. A low allergic response to food from animals with low incidence of viral and bacterial infections is expected under the present theory.

The invention also concerns a device to use in skin tests for immunological responses. In a preferred embodiment, the device is a test unit consisting of a stainless steel disc attached to a handle, preferably a plastic or wooden handle. Projecting from the disc are four triangular-shaped prongs (tines) which are 2 mm long and approximately 4 mm apart. The tines have been mechanically dipped into a solution of Old Para-Tuberculin, containing 7% acacia (gum arabic) and 8.5% lactose as stabilizers, and then dried. The entire unit has been sterilized by Cobalt 60 irradiation. No preservative has been added. Because the unit is disposable; there is no need for syringes, needles, and other equipment necessary for standard intradermal tests. The test can be read in 10 to 15 minutes, or 48 to 72 hours later. The unit can be used more safely than these prior art devices and is expected to result in a lower level of accidental needle sticks than found when syringes with needles are used.

6. EXAMPLES

The following examples are used to illustrate preferred embodiments of the invention and are not meant to limit the scope of the invention in any way.

Case 1:

Congenital Biliary Atresia

An infant, age 3 weeks, weight 6 lbs. (compared to birth weight of 7 lbs.), was critically ill in a hospital with marked jaundice and abnormal liver functions. The diagnosis was congenital biliary atresia, which was substantiated surgically and the Kasai procedure was performed. A liver transplant was scheduled. A clinical strategy was considered in view of the patient's failure to thrive and the harsh planned therapy. Elemental feedings were prescribed.

Specifically, a free L amino acid powdered composition called Neocate (SHS International Ltd., U.K.) was suspended in water at a concentration of approximately 4–6 grams per 1 ounce of water, which translates into approximately 14–16 weight percent of free L amino acid, based on the total weight of the solution. This formulation was administered orally to the infant about 3–4 times a day (about 4–8 hours apart) in 6–8 ounce dosages over the period of about 6–9 months. Foods having exogenous catabolic substrate stimuli, such as all milk products, are avoided.

Unexpectedly, the infant exhibited substantial improvement within 24–48 hours after treatment began. The jaundice rapidly receded and the liver functions improved. The rapid, dramatic clearance of the jaundice, along with the normalization of hepatic laboratory results was a most welcome surprise. The improvement continued throughout the course of treatment. After about three months of treatment, the infant's planned liver transplant was canceled. The liver was diagnosed as healthy, thus confirming that the infant was making a full recovery. The infant rapidly regained the one pound of lost weight and continued normal weight gain, more than doubling her birth weight at six months, and tripling it at one year. At one year, a liver ultrasound showed a completely normal liver. The treatment was no longer necessary after about 6–9 months. Over the course of the next year and a half, the infant showed no signs of relapse and all liver functions remain healthy. This is a dramatic case of unexpected remission of congenital biliary atresia, with the patient no longer requiring transplantation.

Case 2

Anaphylaxis to Renal Dialysis

An adult patient (age 16) had rejected three kidney transplants and was on dialysis. She had severe anaphylaxis to renal dialysis. Initial therapy involves administration of 4–5 capsules daily of L amino acids according to the invention, each capsule containing 390 to 500 mgm essential amino acids in L form and essential lipids. The therapeutic formulation comprises linoleic and linolenic fatty acid for a total amount of about 0.3 to 0.5 g per day, the antioxidant lipid EPA at about 0.3 to 0.5 gram per day, DHA at about 240 mgm per day, and extracellular matrix materials chondroitin sulfate, cartilage, and collagen in a total amount of about 1500 mgm per day. The patient is able to use reduced levels of antirejection medication (such as corticoids, macrolides, and cyclosporin) and thereby reduce the onerous side effects from these medications.

The therapy can also be administered before, during, and after renal transplant to aid in preventing organ rejection.

Case 3

Corneal Transplantation

Patients requiring corneal transplants are prescribed five 390 mgm capsules given three times daily of a therapeutic formulation comprising a composition of the following formulation to mimic cyclosporin: 4 moles L leucine, 2 moles L alanine, 2 moles L valine, 1 mole gamma amino butyric acid, one mole methionine, one mole betaine, and one mole glycine. The formulation further comprises linolenic acid and phospholipids. The therapy is used for the patient's lifetime to minimize lifetime risk of corneal rejection.

Case 4

Kidney Damage

A patient needing kidney transplantation is prescribed a 390 mg capsule comprising L amino acids, linolenic acid, EPA (about 0.3 to 0.5 g per day), and phospholipids, administered as one to five capsules three times daily. The amino acid components are present as essential L amino acids in the molar ratio found in healthy kidney protein.

Case 5

Kidney Failure

A patient needing a kidney transplant receives the therapy of the invention. Five 390 mgm capsules are given three times daily of a formulation comprising linolenic acid, phospholipids, and essential amino acids in the following ratio to mimic cyclosporin: four moles L leucine, two moles L alanine, two moles L valine, one mole methionine, one mole gamma butyric acid, one mole betaine and one mole glycine.

Case 6

Corneal Transplant

A patient receives a corneal transplant. The patient is prescribed 390 mgm capsules to be taken three times daily of a composition comprising linolenic acid, phospholipids, and L amino acids. The L amino acids and their molar ratios are determined based upon a chemical analysis of healthy lens tissue and the diseased lens tissue removed.

Case 7

Chronic Inflammatory Bowel Disease (Regional Ileitus)

A 68 year-old female patient was diagnosed with Crohn's disease (also known as regional ileitus). The diagnosis was made by small bowel barium x-ray. Diagnosis had also been made by surgical removal of seven inches of terminal ileum twenty years ago. The patient received Neocate™ in the form of five capsules containing 390 milligrams each three times a day. This was preceded by a course of 155 milligrams of omega 3 eicosapentanoic acid lipid and 125 mgm DHA administered three times a week for two weeks. The patient had an excellent response with no symptom flare-ups, the absence of side effects attributable to the therapy, and the ability to avoid increasing the dosage of corticosteroids. The patient continued to receive triamcinolone acetate 4 milligrams daily before, during, and after the inventive therapy. In contrast, the patient had needed triamcinolone acetate dosage increases as frequently as every three to four weeks before the inventive therapy was administered. After treatment with the inventive therapy, the patient was able to reduce her average daily corticosteroid dosage by one half. Furthermore, flare-ups were reduced. Thus, the severity of corticosteroid side-effects, such as ecchymoses and bruising, were greatly minimized. The unpleasant taste of the therapeutic compositions was overcome by formulating as capsules. Before meals, 5 capsules of the therapeutic formulation were ingested to allow relief from the extreme discomfort resulting from ingesting dairy products and beef.

Case 8

The patient of Case 7 had the commonly seen complications of long term corticosteroid use, such as recurrent and excessive bruising, particularly of the arms and hands, and difficulty of healing from the mildest trauma. Additional therapy of vitamin K (Mephyton 5 mgm) 4 tablets daily was prescribed. An ointment of Neocate (390 mgm), zinc oxide and vitamin E was prepared, and applied topically to bruises daily with a pressure dressing on any lacerations to accelerate healing.

Case 9

The patient of Case 3 receives the prescribed formulation in the form of ophthalmic preparations in 0.1%, 1.0%, or 5.0% solutions in buffered saline, 1 to 3 drops administered 2 to 3 times daily. Lifetime usage is prescribed.

Case 10

Pericardial Effusion

A 70-year old male was diagnosed by cardiac ultrasound and chest x-ray with pericardial effusion (an autoimmune reaction). He was prescribed a three week regime of the antibiotic Biaxin (500 mg tablet twice daily for persistent bronchitis, Abbott Laboratories, Chicago, Ill.). He was also diagnosed with a false lupus autoimmune reaction to the antibiotic. The patient was removed from all other medications and received the following therapy: cartilage, 2,220 mg capsules daily divided equally to 740 mg taken three times daily; EPA, 360 mg capsules once daily; and omega 3 antiinflammatory fatty acids. In three weeks, his fever and fatigue lessened. His blood sedimentation rate improved dramatically from 75 mm per hour to a normal of 15. His antinuclear antibody (ANA) titer also greatly improved to 1 dilution titer above normal (1:320). His chest x-ray showed no pericardial effusion.

Case 11

Arthritis

A female patient age 45 was diagnosed with traumatic arthritis of the left knee. No response was shown to non-steroidal anti-inflammatory medications. For a limp associated with the arthritis, she was prescribed 740 mg capsules three times daily of chondroitin sulfate collagen cartilage (shark source). After several months of therapy, she has greatly improved and almost free of symptoms. Her chronic bronchitis (which had not responded to a three to four week course of antibiotics) greatly improved in 1–2 days and cleared in one or two weeks when the cartilage dosage described in this case was tripled.

What is claimed is:

1. An anabolic medicament for treating a damaged tissue, the medicament comprising:
   a) at least one extracellular matrix compound in an amount effective in the damaged tissue as anti-inflammatory and anti-neoangiogenetic agent, wherein said extracellular matrix compound is selected from the group consisting of a glycosaminoglycan, a collagen, cartilage, chondroitin sulfate, a glycoprotein, and a proteoglycan;
   b) at least one polar surface active lipid, wherein said polar surface active lipid is selected from the group consisting of a phospholipid, a glycolipid and a lipoprotein; and
   c) a plurality of amino acids having an alpha carbon, the amino acids being present at a molar ratio which is characteristic of human breast milk protein, and wherein no more than 10% of the amino acids are in D-form.

2. The medicament according to claim 1, wherein said extracellular matrix compound is synthetically produced.

3. The medicament according to claim 1, wherein said extracellular matrix compound is obtained from a cellular or tissue source.

4. The medicament according to claim 3, wherein said cellular or tissue source is selected from the group consisting of a cell membrane, a tissue and an organ.

5. The medicament according to claim 1, wherein said polar surface active lipid is obtained from a cellular or tissue source.

6. The medicament according to claim 5, wherein said cellular or tissue source is selected from the group consisting of a cell membrane, a tissue, and an organ.

7. The medicament according to claim 5, wherein at least one extracellular matrix compound, at least one polar surface active lipid, and at least one amino acid associate through a molecular bonding force.

8. The medicament according to claim 7, wherein said molecular bonding force is selected from the group consisting of van der Waals force and ionic interaction.

9. The medicament according to claim 5 further comprising at least one of (a) a mineral; (b) a vitamin; (c) an antioxidant; (d) an omega-3 oil; (e) zinc;(f) zinc oxide; (g) Vitamin A; (h) chondroitin sulfate; (i) cartilage; and (j) collagen.

10. The medicament according to claim 1, wherein said polar surface active lipid is synthetically produced.

11. The medicament according to claim 1, wherein said plurality of amino acids are obtained from a cellular or tissue source.

12. The medicament according to claim 11, wherein said cellular or tissue source is selected from the group consisting of a cell membrane, a tissue, and an organ.

13. The medicament according to claim 1, further comprising a sterile vehicle.

14. The medicament according to claim 1 further comprising at least one of (a) a mineral; (b) a vitamin; (c) an antioxidant; (d) an omega-3 oil; (e) zinc;(f) zinc oxide; (g) Vitamin A; (h) chondroitin sulfate; (i) cartilage; and (j) collagen.

15. The medicament according to claim 1, further comprising gamma amino butyric acid or L-carnitine.

16. The medicament according to claim 1 further comprising a fatty acid selected from the group consisting of linoleic acid and linolenic acid.

17. The medicament of claim 1, wherein the damaged tissue is selected from the group consisting of skin, eye, liver, gastrointestinal organ, kidney, and lung.

18. The medicament of claim 17, wherein the gastrointestinal tissue is bowel tissue.

19. The medicament of claim 18, wherein the bowel tissue is damaged from regional ileitis (Crohn's Disease), inflammatory bowel disease, ulcerative colitis, or mucous colitis.

* * * * *

UNITED STATES PATENT AND TRADEMARK OFFICE
CERTIFICATE OF CORRECTION

PATENT NO. : 6,974,796 B1 Page 1 of 1
APPLICATION NO. : 09/639859
DATED : December 13, 2005
INVENTOR(S) : Leonard S. Girsh It is certified that error appears in the above-identified patent and that said Letters Patent is hereby corrected as shown below:

Title Page

At (76) Inventor, please change the inventor's address form "3360 S. Ocean Blvd., Palm Beach, FL (US) 33480" to --325 Dunes Blvd., Suite 403, Naples, FL 34110--.

Signed and Sealed this

Twenty-sixth Day of December, 2006

JON W. DUDAS
*Director of the United States Patent and Trademark Office*